United States Patent
Mertins et al.

(10) Patent No.: US 10,180,415 B2
(45) Date of Patent: Jan. 15, 2019

(54) SCRIM SUBSTRATE MATERIAL WITH FUNCTIONAL DETECTABLE ADDITIVES FOR USE WITH NONWOVEN FABRIC AND COMPOSITE MATERIAL

(71) Applicant: Illinois Tool Works Inc., Glenview, IL (US)

(72) Inventors: Karen S. Mertins, Lawrenceville, GA (US); Robert Harrison Martin, Gaineville, GA (US)

(73) Assignee: Illinois Tool Works Inc., Glenview, IL (US)

( * ) Notice: Subject to any disclaimer, the term of this patent is extended or adjusted under 35 U.S.C. 154(b) by 85 days.

(21) Appl. No.: 15/262,534

(22) Filed: Sep. 12, 2016

(65) Prior Publication Data

US 2017/0074829 A1    Mar. 16, 2017

Related U.S. Application Data

(63) Continuation-in-part of application No. 15/257,230, filed on Sep. 6, 2016, now abandoned.
(Continued)

(51) Int. Cl.
*G01N 33/36* (2006.01)
*B32B 27/18* (2006.01)
(Continued)

(52) U.S. Cl.
CPC ............ *G01N 33/367* (2013.01); *B32B 5/022* (2013.01); *B32B 5/024* (2013.01); *B32B 5/028* (2013.01); *B32B 5/08* (2013.01); *B32B 5/26* (2013.01); *B32B 27/18* (2013.01); *D04H 3/045* (2013.01); *G01V 5/0016* (2013.01); *G07C 3/146* (2013.01); *B32B 2250/20* (2013.01); *B32B 2262/0215* (2013.01); *B32B 2262/0246* (2013.01); *B32B 2262/0253* (2013.01); *B32B 2262/0261* (2013.01); *B32B 2262/0269* (2013.01); *B32B 2262/0276* (2013.01); *B32B 2262/0292* (2013.01); *B32B 2262/062* (2013.01);
(Continued)

(58) Field of Classification Search
CPC .. G01R 31/40; G01R 31/2841; G01R 31/001; G01R 31/2889; G01L 27/002
USPC .................................... 324/750.01, 500, 537
See application file for complete search history.

(56) References Cited

U.S. PATENT DOCUMENTS 5,793,214 A * 8/1998 Wakamatsu ......... G01N 27/023
324/127
5,897,673 A    4/1999 Nishida et al.
(Continued)

FOREIGN PATENT DOCUMENTS

JP    2008303525 A    12/2008

*Primary Examiner* — Giovanni Astacio-Oquendo
(74) *Attorney, Agent, or Firm* — Avery N. Goldstein; Blue Filament Law PLLC

(57) ABSTRACT

An article is provided with a web of polymer fibers forming a scrim with openings between the polymer fiber elements. A particulate is distributed in, or on the polymer fiber in a quantity to make the scrim detectable by X-ray detection or magnetic detection. One or more layers are laminated to the scrim. A process for detecting a multi-layered laminated scrim-containing article with magnetic or X-ray detection equipment in a production setting is also provided. With process implementation article loss in a product can be detected thereby reducing precautionary product discard.

19 Claims, 1 Drawing Sheet

Related U.S. Application Data

(60) Provisional application No. 62/218,570, filed on Sep. 15, 2015.

(51) Int. Cl.
- *B32B 5/02* (2006.01)
- *B32B 5/26* (2006.01)
- *G01V 5/00* (2006.01)
- *G07C 3/14* (2006.01)
- *D04H 3/045* (2012.01)
- *B32B 5/08* (2006.01)

(52) U.S. Cl.
CPC ..... *B32B 2262/12* (2013.01); *B32B 2264/102* (2013.01); *B32B 2264/105* (2013.01); *B32B 2305/38* (2013.01); *B32B 2307/726* (2013.01); *B32B 2311/30* (2013.01); *B32B 2432/00* (2013.01); *B32B 2437/00* (2013.01)

(56) References Cited

U.S. PATENT DOCUMENTS

| | | | |
|---|---|---|---|
| 7,222,727 B2 | 5/2007 | Aisenbrey | |
| 7,242,176 B2* | 7/2007 | Thomason | G01R 31/002 324/501 |
| 7,952,375 B2* | 5/2011 | Eldridge | G01R 1/06711 324/754.03 |
| 8,093,161 B2* | 1/2012 | Bansal | D01F 8/06 442/334 |
| 8,410,006 B2* | 4/2013 | Chappas | B01D 39/04 428/364 |
| 8,980,982 B2 | 3/2015 | Martin et al. | |
| 9,303,342 B2* | 4/2016 | Wang | B32B 5/08 |
| 2005/0153857 A1 | 7/2005 | Sherry et al. | |
| 2007/0219516 A1 | 9/2007 | Patel et al. | |
| 2010/0087731 A1 | 4/2010 | Ramachandran | |
| 2015/0132574 A1 | 5/2015 | Aldridge et al. | |

\* cited by examiner

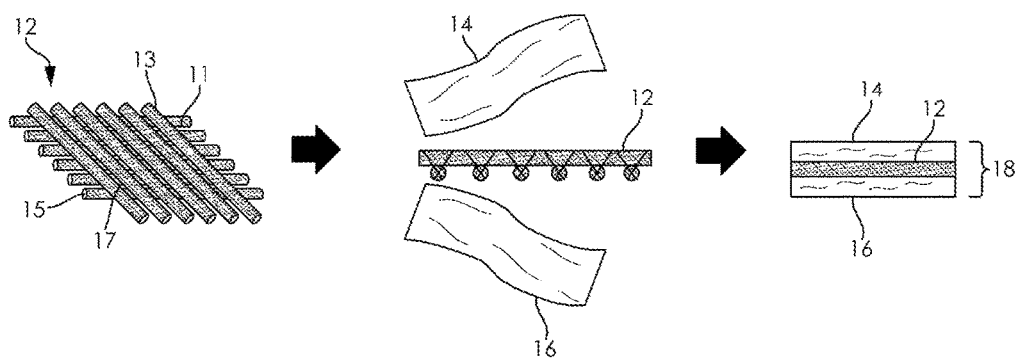
FIG. 1A  FIG. 1B  FIG. 1C

SCRIM SUBSTRATE MATERIAL WITH FUNCTIONAL DETECTABLE ADDITIVES FOR USE WITH NONWOVEN FABRIC AND COMPOSITE MATERIAL

CROSS REFERENCE TO RELATED APPLICATIONS

This application is a continuation of U.S. application Ser. No. 15/257,230 filed 6 Sep. 2016 that in turn claims priority benefit of U.S. Provisional Application Ser. No. 62/218,570 filed 15 Sep. 2015; the contents of which are hereby incorporated by reference.

FIELD OF THE INVENTION

The present invention relates to the technical field of polymeric composite fibers, and in particular to a scrim material formed with polymeric fibers with high loadings of metal or other particulate that render articles formed from such fibers X-ray or magnetic detectable.

BACKGROUND OF THE INVENTION

Servicing of a food or pharmaceutical production line currently has strict guidelines that require exclusion zones from which various material packaging components and accessories are excluded. In spite of these exclusion policies, plastic debris does enter production lines and with even a single piece of plastic entering a production stream, large quantities of otherwise usable product must be discarded. Rules regarding processing of ground meat are exemplary of those that require discard of the product if possibly contaminated. Common plastic packaging or service articles that are inadvertently brought into production exclusion zones include aerosol cans, grease cartridge tubes, grease tube caps, plastic fiber toweling, packing straps, pail lids, jar caps, and personal protective clothing.

Metal detectors are commonly found on food processing lines to assure that metal shards that represent a laceration hazard do not end up in food products. Similarly, pharmaceutical and biomedical device production are also vulnerable to not only the hazards associated with metal debris ending up in product streams, but also the prospect that such metal can degrade active pharmaceutical ingredients or serve as a potential source of infection. Numerous technologies are known to the art to detect spurious metal within a production line. These technologies include a transmitter coil-receiver coils for metal detection systems, systems that use radio frequencies, and magnetic field based systems. In recognition of the fact that some metallic materials are not ferromagnetic and simultaneously not particularly good electrical conductors, x-ray scanners and other electromagnetic field (emf) spectral region spectral detection techniques have been added to food and pharmaceutical product lines to facilitate the detection of a wider range of contaminants.

Many industries have a need for metal detectable polymers and articles made therefrom. By way of example, a food, medical, or pharmaceutical production line maintains tight audit control of service items that enter the manufacturing facility to assure such items do not accidently enter the production stream as a contaminant that can be fragmented into dangerous shards. Historically, plastics have been precluded from some environments due to the inability to locate such articles with product screening X-ray or magnetic detectors. Recently, plastic articles have been developed that are filled with metal particulate or barium sulfate, as detailed in U.S. Pat. No. 8,980,982 that are detectable with magnetic or X-ray detectors, yet still process as injection moldable thermoplastics and operate in a manner similar to their unfilled conventional counterparts.

By way of example, U.S. Pat. No. 5,897,673 teaches fibers containing fine metallic particles that are cross-linked to the polymeric fiber. While various pure metals are contemplated in the literature, little attention has been paid to the unique problems associated with stainless steel particulate. As many foods and manufactured substances can only be exposed to stainless steel, the lack of stainless steel particle filled fibers precludes the usage of many useful articles from these controlled manufacturing sites. By way of example various wipes, scrub pads, hair covers, suits, aprons and shoe covers and other manufacturing aids or personal protective equipment if made from stainless steel containing fibers could allow better quality control of manufacturing with less stringent audit processes as any such articles lost in a production stream could be detected by X-ray or magnetic anomaly.

Thus, there exists a need for a thermoplastic fiber filled scrim structure with detectable particulate or functional additives. There also exists a need for such fibers that process and retain properties of conventional thermoplastic fibers to promote production of various articles from fibers that have the added benefit of being X-ray or magnetically detectable while operating in a manner similar to conventional articles.

SUMMARY OF THE INVENTION

An article is provided with a web of polymer fibers that each have a cross-section and a length arranged as bi-directional elements each with an element width and defining openings between intersecting elements. The openings having an opening width greater than the element width of contiguous elements to the opening to form a scrim having a first surface and a second surface in opposition to the first surface. A particulate distributed is in, or on the polymer fiber in a quantity to make the scrim detectable by X-ray detection or magnetic detection. One or more layers are laminated to at least the first surface of the scrim. A scrim or web material made from polymer containing functional additives, and other additives is provided, where the scrim may be used as a substrate for nonwoven fabric or other laminated engineered materials. The particulate additives are incorporated into the polymer prior to web formation, and may be manufactured by any of several means commercially known such as injection molding, extrusion, weaving extruded filaments, or thermally bonding laid scrim, or by methods currently unknown. Properties imparted to the scrim materials may include electromagnetic spectral detectability, thereby making articles incorporating the scrim suitable for usage in a variety of fields including food production, medical, and pharmaceutical production environments.

A process for detecting a multi-layered laminated scrim-containing magnetically or X-ray detection equipment in a production environment is also provided. With process implementation article loss in a product can be detected thereby reducing precautionary product discard.

BRIEF DESCRIPTION OF THE DRAWINGS

The present invention is further detailed with respect to the following figures that depict various aspects of the present invention.

FIGS. 1A-C illustrate the sequential formation of a multi-layered laminated scrim-containing fabric with functional additives in accordance with embodiments of the invention.

DETAILED DESCRIPTION OF THE PREFERRED EMBODIMENTS

The present invention has utility as a scrim or web material made from polymer containing functional additives, and other additives, where the scrim may be used as a substrate for nonwoven fabric or other laminated engineered materials. Embodiments of the base web material forming the scrim may have properties imparted by the various functional additives that are incorporated into the polymer prior to web formation, and may be manufactured by any of several means commercially known such as injection molding, extrusion, weaving extruded filaments, or thermally bonding laid scrim, or by methods currently unknown. Properties imparted to the scrim materials may include electromagnetic spectral detectability, thereby making the scrim suitable for usage in a variety of fields including food production, medical, and pharmaceutical production environments.

Embodiments of the inventive detectable scrim may be used independently or fashioned into a laminated material by the addition of one or more layers of secondary materials. A non-limiting illustrative example of an embodiment of a laminated composite material is a metal detectable scrim layered between a face and back layer of absorbent fibers. A specific inventive example is a hydroentangled hybrid wipe composed of extruded metal detectable scrim bound to wet laid absorbent fiber layers resulting in a wiping cloth which is both absorbent and metal detectable. The nonwoven engineered wipe is both absorbent and metal detectable making it employable for various wiping applications such as personal hygiene, equipment and parts cleaning in food processing critical environments.

It is noted that the innovative detectable scrim by itself would not have the characteristics of a wipe. By layering the scrim with other components a useful wipe may be fashioned. The laminated material allows multiple functionalities in a single product.

As used herein, the term "fiber" defines both fibers of finite length, such as conventional preselected length fiber, as well as substantially continuous structures, such as continuous filaments, unless otherwise indicated. The fibers of the present invention are appreciated to be hollow or solid fibers, and further can have a substantially round or circular cross-section or cross-sections of different symmetry space groups with other cross-sections illustratively including oval; lobular; polygonal such as triangular, square, rectangular, trapezoidal, pentagonal, and hexagonal. A fiber of the present invention in some embodiments has a sheath that varies in polymer or particulate, with the variation being as to composition or concentration, or both such properties.

As used herein, the term "multi-component fibers" is defined to include preselected length fiber and continuous filaments with two or more discrete structured domains of deliberately different composition or component concentration and is intended to specifically include sheath/core and island configurations.

As used herein, the term "yarn" defines multiple fibers wound together into a single continuous strand.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

It is appreciated that both the cross-sectional shape of the fiber and the configuration of the particulate and other components therein depends upon the equipment that is used in the preparation of the fiber, the process conditions, and the melt viscosities of the various components. A wide variety of fiber configurations are readily produced according to the present invention to achieve loadings sufficient for magnetic or X-ray detection.

The polymeric component of the fiber is readily selected from any of the types of polymers known in the art that are capable of being formed into fibers, including polyolefins, polyvinyl, polyvinyl alcohol, polyesters, polyamides, copolymers containing any of the aforementioned polymers as blocks of a copolymer, and combinations thereof. Specific polyolefins operative herein illustratively include polypropylene; polyethylene; polybutene; and polyisobutylene; polyamides such as NYLON 6 and NYLON 6,6; polyacrylates; polystyrenes; polyurethanes; acetal resins; polyethylene vinyl alcohol; polyesters such as polyethylene terephthalate (PET), polyethylene naphthalate, polytrimethylene terephthalate, poly(1,4-cyclohexylene dimethylene terephthalate) (PCT), polycarbonates; and aliphatic polyesters such as polylactic acid (PLA); polyphenylene sulfide; thermoplastic elastomers; polyacrylonitrile; cellulose and cellulose derivatives; polyaramids; acetals; fluoropolymers; copolymers and terpolymers thereof and mixtures or blends thereof, and without regard as whether a given polyolefin is syndiotacic, eutectic, isotactic, or atactic.

Specific examples of aliphatic polyesters operative in the present invention include fiber forming polymers formed from a combination of an aliphatic glycol such as ethylene glycol, propylene glycol, butylene glycol, hexanediol, octanediol or decanediol) or an oligomer of ethylene glycol (e.g., diethylene glycol or triethylene glycol) with an aliphatic dicarboxylic acid such as succinic acid, adipic acid, hexanedicarboxylic acid or decaneolicarboxylic acid); or the self-condensation of hydroxy carboxylic acids other than poly(lactic acid), such as polyhydroxy butyrate, polyethylene adipate, polybutylene adipate, polyhexane adipate, and copolymers containing the same. Aromatic polyesters operative in the present invention include fiber forming polymers formed from polyesters of alkylene glycols having 2-10 carbon atoms and aromatic diacids; polyalkylene naphthalates, which are polyesters of 2,6-naphthalenedicarboxylic acid and alkylene glycols, as for example polyethylene naphthalate; or polyesters derived from 1,4-cyclohexanedimethanol and terephthalic acid, as for example polycyclohexane terephthalate. Exemplary polyalkylene terephthalates include polyethylene terephthalate (also PET) and polybutylene terephthalate.

In some inventive embodiments that are compliant with food, medical and pharmaceutical processing standards, the particulate is stainless steel. Other compositions of particulate to render an inventive fiber magnetic or X-ray signal detectable include iron, bronze, brass, steel, barium salts, cobalt, titanium, tin, copper, tungsten, platinum, silver, bismuth, zinc, lead, molybdenum, neodymium, samarium, alloys of any of the aforementioned, oxides of any of the aforementioned metals, nitrides of any of the aforementioned. It is appreciated that cobalt alloys such as cobalt-samarium, and neodymium alloys have exceptionally high magnetic moments that allow for magnetic detection at lower weight loading compared for ferrite. In some inventive embodiments, the stainless steel is ferromagnetic and detectable by magnetic induction coil detectors. Specific grades of stainless particulate operative herein include 300 series, 400 series and in particular 306 (L), 316 and 430 compositions The present invention attempts to retain the processing and performance properties of the native polymer while imparting the ability to render the fiber and articles formed therefrom X-ray or magnetic anomaly detectable. This is achieved by inclusion of particulate having a shortest linear dimension, as measured from among the three orthogonal Cartesian coordinate axes X-Y-Z that is less than or equal to one half the fiber cross-sectional average dimension along the three orthogonal Cartesian coordinate axes X-Y-Z. For the purposes of calculation of the particulate dimension, the average particle dimension is used for polydisperse particulate. By way of example, a circular cross-section fiber with a diameter of 35 microns is loaded with spherical particulate having a diameter of less or equal to 17 microns. In some inventive embodiments containing cylindrical rod particulate, the ratio of rod length to diameter is between 1.3-20:1 and in still other embodiments between 1.5-8:1

In certain embodiments, each of the polymeric components of an inventive fiber includes other substances known conventionally to modify a processing property or performance property. Such additive substances illustratively include antioxidants, stabilizers, surfactants, waxes, flow promoters, solid solvents, dyes, pigments, plasticizers and combinations thereof. It is appreciated that a pigment can encompass a composition of a particulate material detailed above to impart detectability to the inventive fiber and in such instances the pigment is compositionally distinct from the particulate and present in a lower weight percentage than the particulate.

It is appreciated that the loading of particulate to achieve X-ray or magnetic detection of articles formed from inventive fibers is dictated by factors including the X-ray cross-section or the magnetic susceptibility of a given particulate. Generally, ferromagnetic materials are detectable at loadings of from >2 total weight percent by magnetic induction detection. In those embodiments when the ferromagnetic material is a rare earth magnet, typical loadings are from 2 to 4 total weight percent for magnetic induction detection. In specific embodiments where the particulate is magnetic stainless steel or any other electromagnetic spectrally detectable particulate, typical loadings are from 5 to 50 total weight percent for magnetic induction detection. It is appreciated that the above typical loading can be exceeded, yet often at the expense of detrimentally influencing processibility or increasing material financial costs with only incremental improvements in detection.

The continuous filaments in certain inventive embodiments are mechanically crimped and cut into a desirable fiber length, thereby producing staple fiber. The length of the staple fibers typically ranges from 25 to 50 millimeters, although the fibers can be cut to any desired length outside this range.

The multi-component fibers of the invention can be staple fibers, continuous filaments, or meltblown fibers. In general, staple fibers, multifilament, and spunbond fibers formed in accordance with the present invention can have a fineness of 0.1 to 500 microns per filament. Meltblown filaments can have a fineness of 0.1 to 500 microns. Monofilament fibers can have a fineness of 0.1 to 500 microns.

The multi-component fibers of the invention are useful in the production of a wide variety of products, including without limitation nonwoven structures, such as but not limited to scrims used in forming carded webs, wet laid webs, dry laid webs, spunbond webs, meltblown webs, and the like. The nonwoven webs can be bonded to transform the webs into a coherent nonwoven fabric using bonding techniques known in the industry. Exemplary bonding techniques for nonwoven webs include mechanical bonding, such as hydro-entanglement and needle punching, adhesive bonding, thermal bonding, and the like. An example of thermal bonding is through air bonding, although other thermal bonding techniques, such as calendaring, microwave or other RF treatments are readily employed.

A characteristic of a scrim according to the present invention is the presence of openings between the fibers that bound the opening. The fibers bounding an opening are referred to synonymously as elements. The openings have a width greater that the width of the bounding elements. It is appreciated that the fibers can be woven or non-woven or even random as still form a bi-directional web inclusive of such openings.

In some inventive embodiments, the inventive fibers are subjected to a coating, laminate, or otherwise cover the outer and/or inner surfaces of threads or layers of material contained within any final product without falling outside the scope of the invention. In the context of a scrim, these correspond to a first surface and a second surface in opposition to the first surface. This is a practice well known to those experienced in the art, and is commonly used to impart non-stick, low-friction, or additional chemical and heat resistance properties to the final product. It is appreciated that additional non-polymeric particles identical, similar, or fundamentally different to the particles already contained within the composite fibers of the invention are readily added to the fibers. Such additions can come, at the expense of lowering the overall metal content loading of the resultant article.

In certain embodiments of the present invention a fiber or core portion of a sheathed fiber has particulate protruding from the wall of the fiber and a concomitant relative depletion of particulate from the central region of a fiber. The inclusion of a particulate protrusions and centrally depleted fiber region has been found to afford considerable benefits in increasing the loading amount of particulate to detectable levels and the energy needed to slide fibers past one another.

In some embodiments of the present invention, following extrusion but prior to coating or lamination, the fibers or other non-woven creations of the invention are coated, dusted, or otherwise induced to carry on the exterior of individual filaments or layers additional particulate identical, similar, or fundamentally different to the particulate already contained within the composite fibers of the invention.

Particulate is most easily adhered to the outside of the fibers using a process which passes the extruded filament or non-woven creation through an enclosed chamber, in which a fan system lifts and circulates the particulate throughout the air contained within the chamber such that a fraction of the particles that contact the filament will adhere to the surface.

In another embodiment of the invention, the fibers of the invention are used to weave or knit a scrim. In addition, an inventive scrim is laminated to a woven, knit, or non-woven fabric layer.

In yet another embodiment of the invention, custom composite fibers of the invention are woven or otherwise used in the construction of fabric or fabric-like structures. The fabric performs comparably to standard polymer containing fabrics with respect to most attributes, such as strength, durability, and hand, yet like the fibers exhibits properties which deviate significantly from those normally associated with the polymeric material by those experienced in the art, these unique properties beside detectability illustratively include high density, conductivity, electromagnetic shielding, cut-resistance, heat-resistance, and radiation shielding relative to the base polymer absent particulate loading.

Modern metal detection is based on creating a magnetic field with a transmitter coil and two receiving coils wired in reverse. The resulting field is interrupted when a conductive or magnetic contaminant passes through the field. The contaminant is detected by measuring the change in voltage above the change in voltage of non-contaminated product. If a contaminant is detected, that product is rejected. Contaminants are generally categorized as sphere equivalents in millimeters. The sensitivity and throughput are machine dependent.

X-ray inspection is based on density. The higher the density of the object being examined; the more energy is absorbed. X-ray detection measures how much energy is absorbed by a product or contaminant. X-ray detection can detect contaminants such as glass or bone that a metal detector will not detect. X-ray detection can perform other quality functions outside the scope of product contamination. The present invention focuses on contaminant detection. The contaminants are generally categorized as sphere equivalents. The sensitivity and throughput are machine dependent. In a production setting, the X-ray detector or the magnetic detector is associated with a production line that can be stopped when an inventive scrim is detected by way of detector signal in the production stream. As a result, the effects of the contamination event are mitigated. Alternatively, a rejected product is shunted from the production line in response to the positive detector signal of contaminant being present.

FIGS. 1A-C illustrate a process 10 for the formation of a multi-layered laminated scrim-containing structure 18 with functional additives in accordance with embodiments of the invention. At FIG. 1A, a scrim 12 is formed from a web of functional polymer formed as fiber elements 11. The scrim 12 has a first surface 13 and a second opposing surface 15. Openings 17 are defined by bounding fiber elements 11. An opening 17 has a width greater than that of any of the bounding fiber elements 11. At FIG. 1B, an upper layer 14 and a lower layer 16 are introduced and laminated to the scrim 12 (FIG. 1C) to form a multi-layered laminated scrim-containing structure 18. The upper layer 14 and lower layer 16 may be made of the same or of different materials, and illustratively may include functional or nonfunctional fibers.

The following example specific non-limiting examples of present invention. These examples should not be considered to be a limit on the scope of the appended claims.

Example 1

Spherical stainless steel particulate (430 series) having a Poisson size distribution and an average particle size of 12 microns is mixed into polypropylene (PP) to form pellets with a particulate loading of 12 percent. The particles are melt-spun and the melt is then drawn to a fiber. Some of the particulate is noted to be flattened or misshaped. The resulting fibers where formed into a scrim and subjected to metal detector response on a Loma IQ$^3$+ balanced coil metal detector alone or with various food products of a box of 8 packages of crackers, or frozen pizza in a cardboard box. The results are provided in Table 1 for various sizes and fold configurations of scrim. The values in millivolts for triplicate repeats with the threshold detections being noted. All sample pieces were cut with longest dimension oriented in machine direction

TABLE 1

Data for 12% by weight stainless steel particles in PP scrim, data in millivolts (mV),

| | Sample Size (in.) | | | | | | | | | | | | |
|---|---|---|---|---|---|---|---|---|---|---|---|---|---|
| | 1 × 2 | | 2 × 2 | | 3 × 2 | | 3 × 4 | | 6 × 2 | | 6 × 4 | | |
| | Sample Orientation | | | | | | | | | | | | |
| | Perpendicular | Parallel | Machine direction parallel | Machine direction perpendicular | Perpendicular | Perpendicular | Perpendicular | Parallel | Perpendicular | Parallel | Folded Perpendicular | Folded Parallel | Perpendicular | Parallel |
| Mode | 78 | 96 | 122 | 124 | 123 | 129 | 262 | 396 | 459 | 160 | 154 | 254 | 110 | 412 |
| QC (dry) | 63 | 710 | 139 | 118 | 120 | 146 | 278 | 346 | 505 | 187 | 137 | 217 | 110 | 398 |
| Threshold = 100 | 114 | 97 | 112 | 132 | 104 | 141 | 276 | 309 | 467 | 184 | 179 | 245 | 102 | 384 |
| Mode | 52 | 87 | 91 | 85 | 82 | 175 | 227 | 219 | 496 | 145 | 111 | 181 | 136 | 389 |
| Crackers (wet) | 75 | 50 | 80 | 140 | 64 | 225 | 267 | 223 | 492 | 168 | 92 | 182 | 135 | 384 |
| Threshold = 100 | 46 | 63 | 90 | 70 | 102 | 161 | 248 | 263 | 477 | 177 | 84 | 211 | 141 | 397 |
| Mode | 1264 | 1855 | 2447 | 2365 | 2219 | 2575 | 5288 | 5395 | 8076 | 3656 | 2478 | 3904 | 304 | 5433 |
| Pizza (wet) | 1267 | 1845 | 2500 | 2381 | 2257 | 2619 | 4980 | 5352 | 7640 | 3585 | 2677 | 3925 | 1279 | 5179 |
| Threshold = 275 | 1284 | 1849 | 2467 | 2385 | 2204 | 2786 | 5136 | 5409 | 7454 | 3497 | 2729 | 3775 | 1296 | 5115 |

TABLE 2

Continued data for scrim, data in millivolts (mV).

| | Sample Size (in.) | | | | | | | | | | | | | | |
|---|---|---|---|---|---|---|---|---|---|---|---|---|---|---|---|
| | 6 × 4 | | | 6 × 6 | | | 3 × 8 | | | | | | 6 × 8 | | | |
| | | | | | | | Sample Orientation | | | | | | | | | |
| | Folded Perpendicular | Folded Parallel | Square | Folded Perpendicular | Folded parallel | Twice Folded Square | Perpendicular | Parallel | Folded Perpendicular | Folded Parallel | Perpendicular | Parallel | Folded Perpendicular | Folded Parallel | Twice Folded Perpendicular | Twice Folded Parallel |
| Mode | 200 | 344 | 253 | 208 | 5972 | 6904 | 100 | 483 | 297 | 516 | 259 | 415 | 429 | 3426 | 4048 | 14642 |
| QC (dry) | 222 | 373 | 242 | 218 | 6069 | 7068 | 79 | 455 | 254 | 530 | 203 | 382 | 444 | 3354 | 3719 | 14679 |
| Threshold = 100 | 201 | 378 | 235 | 246 | 5915 | 7105 | 102 | 427 | 301 | 520 | 224 | 348 | 464 | 3387 | 4331 | 14735 |
| Mode Crackers (wet) | 177 | 389 | 287 | 265 | 4830 | 3177 | 202 | 644 | 247 | 547 | 446 | 463 | 30 | 1677 | 1940 | 11832 |
| | 185 | 386 | 261 | 264 | 4714 | 3217 | 193 | 599 | 238 | 544 | 433 | 466 | 417 | 1724 | 1444 | 11900 |
| Threshold = 100 | 191 | 369 | 267 | 285 | 4821 | 3357 | 196 | 606 | 226 | 574 | 567 | 461 | 415 | 1538 | 1546 | 12053 |
| Mode Pizza (wet) | 3668 | 6007 | 4003 | 4330 | 15343 | 15517 | 1877 | 6956 | 5363 | 9142 | 304 | 524 | 719 | 8376 | 8652 | 20537 |
| | 3724 | 6041 | 4118 | 4428 | 14663 | 15469 | 1861 | 6727 | 5483 | 9025 | 305 | 534 | 696 | 8354 | 8483 | 20509 |
| Threshold = 275 | 3758 | 6047 | 4079 | 4522 | 14097 | 15057 | 1835 | 7256 | 5406 | 8907 | 306 | 463 | 718 | 8304 | 8602 | 20534 |

TABLE 3

Ferrous sphere size equivalent for scrim where the metal detector was set to wet conductive product with phase out point of ~90°.

| | ~Fe Sphere Equivalent (wet mode frozen) | | | | | |
|---|---|---|---|---|---|---|
| Size (in.) | Perpendicular | Parallel | Folded Perpendicular | Folded Parallel | Folded Twice Perpendicular | Folded Twice Parallel |
| 1 × 2 | 1.0 mm | 1.0 mm | N/A | N/A | N/A | N/A |
| 2 × 2 | 1.0 mm | N/A | N/A | N/A | N/A | N/A |
| 3 × 2 | 1.0 mm | 1.0 mm | N/A | N/A | N/A | N/A |
| 3 × 4 | 1.5 mm | 1.5 mm | N/A | N/A | N/A | N/A |
| 6 × 2 | 1.5 mm | 1.5 mm | 1.5 mm | 1.5 mm | N/A | N/A |
| 6 × 4 | 1.0 mm | 1.5 mm | 1.0 mm | 1.5 mm | N/A | N/A |
| 6 × 6 | 1.5 mm | N/A | 2.0 mm | 1.5 mm | 2.0 mm | N/A |
| 3 × 8 | 1.0 mm | 1.5 mm | 1.5 mm | 1.5 mm | N/A | N/A |
| 6 × 8 | 0.8 mm | 0.8 mm | 0.8 mm | 1.5 mm | 1.5 mm | 2.5 mm |

The foregoing description is illustrative of particular embodiments of the invention, but is not meant to be a limitation upon the practice thereof. The following claims, including all equivalents thereof, are intended to define the scope of the invention.

The invention claimed is:

1. An article comprising:
a web of polymer fibers having a cross-section and a length arranged as bi-directional elements each with an element width and defining openings between intersecting elements with each opening having an opening width greater than the element width of contiguous elements to each opening to form a scrim having a first surface and a second surface in opposition to the first surface; and
a particulate distributed in said polymer fiber in a quantity to make said scrim detectable by X-ray detection or magnetic detection; and
one or more layers laminated to at least the first surface of said scrim.

2. The article of claim 1 wherein said particulate is stainless steel.

3. The article of claim 1 wherein said particulate having a shortest linear dimension as measured from among three orthogonal Cartesian coordinate axes X-Y-Z that is less than or equal to one half a cross-sectional average dimension of said polymer along the three orthogonal Cartesian coordinate axes X-Y-Z.

4. The article of claim 1 wherein said particulate is one of: iron, bronze, brass, steel, barium salts, cobalt, titanium, tin, copper, tungsten, platinum, silver, bismuth, zinc, lead, molybdenum, neodymium, a samarium, an alloy of any one of the aforementioned metals, an oxide of any one of the aforementioned metals, a nitrides of any one of the aforementioned metals.

5. The article of claim 1 wherein said particulate are flattened spheroids.

6. The article of claim 1 wherein said polymer fiber is formed is one of polypropylene, polyethylene, polybutene, polyisobutylene, a polyamide, a polyacrylate, a polystyrene, a polyurethane, an acetal resin, a polyethylene vinyl alcohol; a polyester, a polyphenylene sulfide, a thermoplastic elastomers, a polyacrylonitrile; a cellulose, a polyaramid, or a block copolymer containing at least one of the aforementioned.

7. The article of claim 1 wherein the first surface and the second surface of said scrim are both in contact with layer of absorbent fibers exterior to said scrim.

8. The article of claim 1 further comprising a sheath surrounding said polymer fiber.

9. The article of claim 1 wherein said polymer fiber has a diameter between 0.1 and 500 microns.

10. The article of claim 1 wherein said particulate is present from 2 to 50 total weight of said polymer fiber.

11. The article of claim 1 wherein said particulate forms protrusions on said polymer fiber.

12. A process of detecting a fabric article comprising:
forming a fiber comprising a polymer having a cross-section and a length, and a particulate distributed in said polymer to form protrusions;
forming a scrim from a web of said fibers arranged as bi-directional elements each with an element width and defining openings between intersecting elements with each opening having an opening width greater than the element width of contiguous elements to the opening, said scrim having a first surface and a second surface in opposition to the first surface;
manufacturing a laminated article from said scrim;
passing the laminated article through an X-ray detector or a magnetic detector; and
collecting a signal from said X-ray detector or said magnetic detector indicative of the presence of the laminated article.

13. The process of detecting the laminated article of claim 12 wherein said laminated article is a wipe.

14. The process of detecting the laminated article of claim 12 wherein said laminated article is a scrub pad.

15. The process of detecting the laminated article of claim 12 wherein said scrim is non-woven.

16. The process of detecting the laminated article of claim 12 wherein said polymer fiber is sheathed.

17. The process of detecting the laminated article of claim 16 further comprising stopping said production line in response to the signal.

18. The process of detecting the laminated article of claim 16 further comprising shunting product as rejected in response to the signal from said production line.

19. The process of detecting the laminated article of claim 12 wherein said X-ray detector or said magnetic detector is associated with a production line.

* * * * *